United States Patent [19]

Orandi

[11] Patent Number: 4,524,770
[45] Date of Patent: Jun. 25, 1985

[54] ENDOSCOPE INJECTION NEEDLE

[76] Inventor: Ahmad Orandi, Rte. 6, Box 138A, Fergus Falls, Minn. 56537

[21] Appl. No.: 460,873

[22] Filed: Jan. 25, 1983

[51] Int. Cl.³ ............................................. A61B 17/39
[52] U.S. Cl. ............................ 128/303.1; 128/303.18; 604/160
[58] Field of Search ... 128/4, 6, 303.1, 303.13–303.15, 128/303.18, 783, 784; 604/160, 161, 163, 164, 171, 172

[56] References Cited

U.S. PATENT DOCUMENTS

| | | | |
|---|---|---|---|
| 3,620,500 | 11/1971 | Santomieri | 604/280 X |
| 3,682,162 | 8/1972 | Colyer | 128/303.18 X |
| 3,834,392 | 9/1974 | Lampman et al. | 128/4 X |
| 4,237,871 | 12/1980 | Bonnet | 128/4 |

FOREIGN PATENT DOCUMENTS

| | | | |
|---|---|---|---|
| 628292 | 10/1961 | Canada | 604/160 |
| 2922511 | 12/1980 | Fed. Rep. of Germany | 128/4 |
| WO82/02488 | 8/1982 | PCT Int'l Appl. | 128/303.14 |

OTHER PUBLICATIONS

ACMI Urology Catalog, no date.
"VPI Needles", no date.

Primary Examiner—Edward M. Coven
Attorney, Agent, or Firm—Merchant, Gould, Smith, Edell, Welter & Schmidt

[57] ABSTRACT

The present invention is directed to an attachment tool (10) for use with an endoscopic instrument (30). Instrument (30) includes a working element (74) having a mechanism (28) for clamping an accessory such as tool (10). Tool (10) includes a hollow needle (12) attached to a hollow shaft (14). A flexible tube (16) passes through shaft (14) to provide fluid communication between a syringe mechanism and needle (12). End element (18) has portion (34) which is held by clamping mechanism (28). An electrical path is provided by wire (20) between element (18) and needle (12) whereby tool (10) may function not only as an injection needle but as a needle electrode.

2 Claims, 8 Drawing Figures

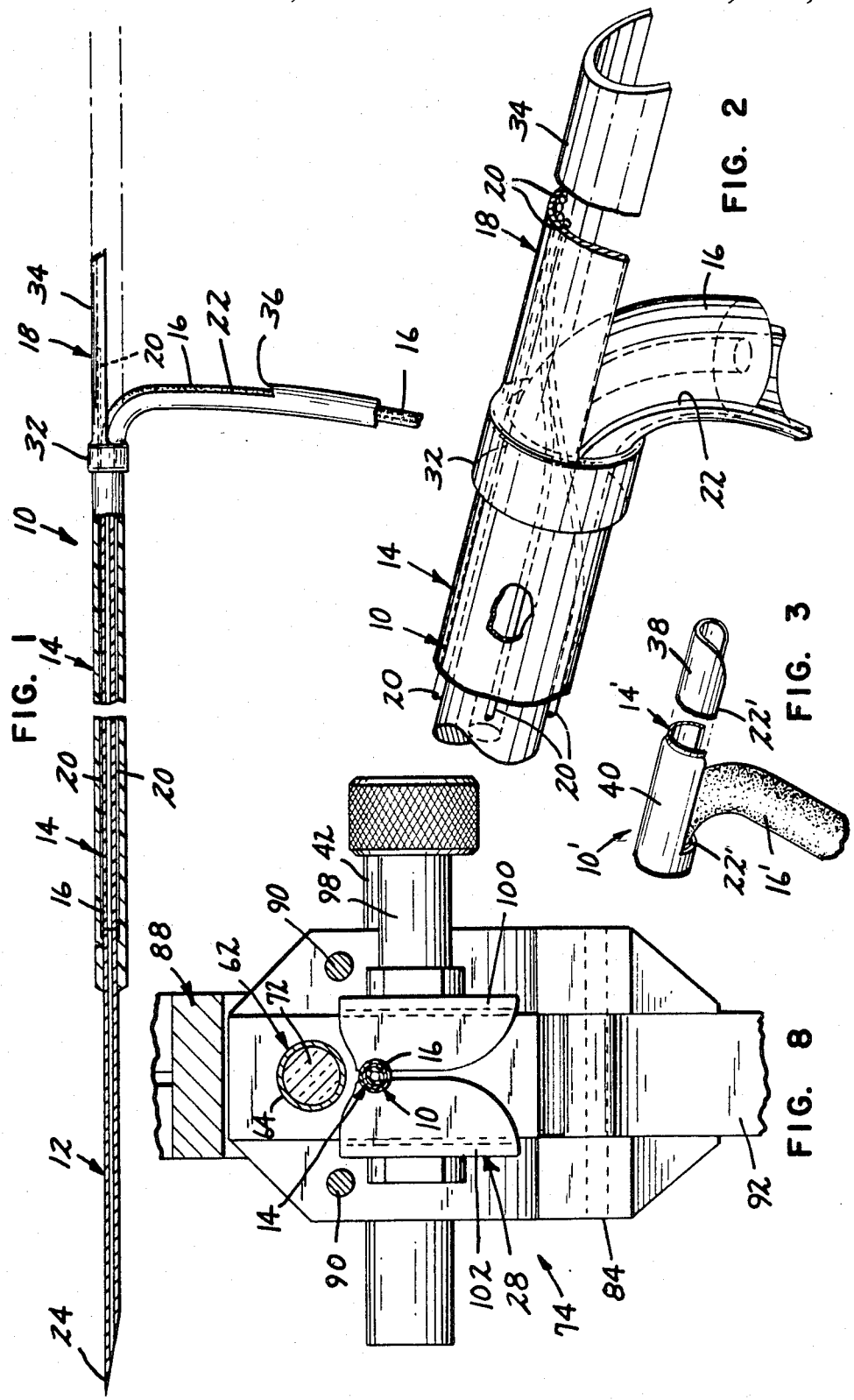

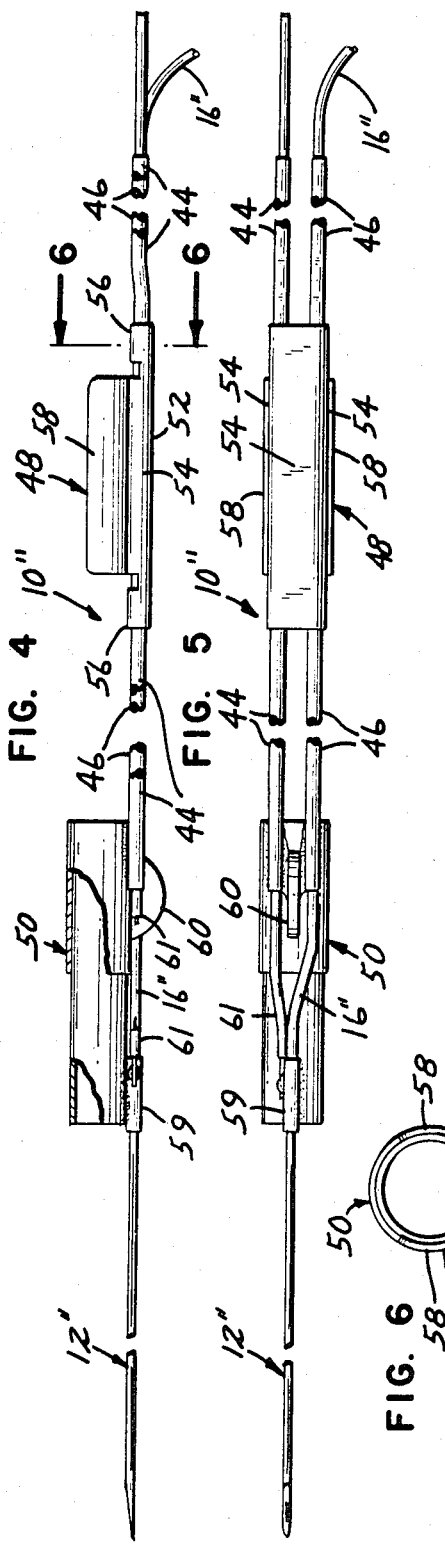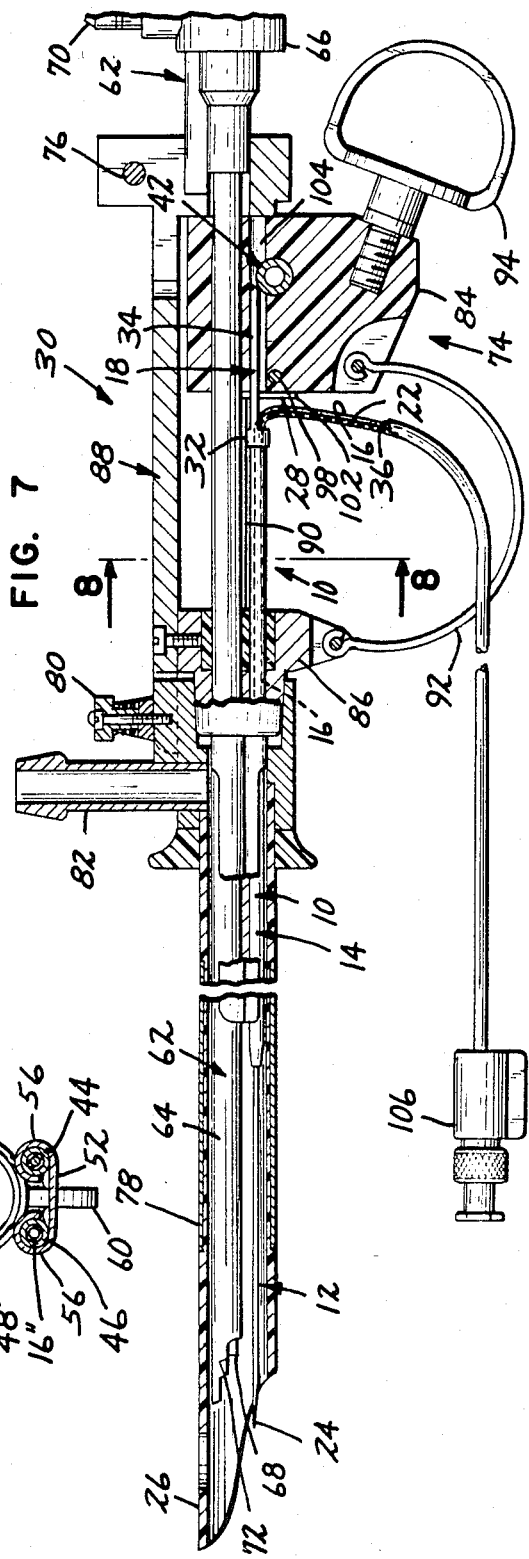

ENDOSCOPE INJECTION NEEDLE

This invention relates to the general field of endoscopic instruments. More particularly, the invention relates to an attachment tool, that is, an injection needle, and alternatively, an injection needle-electrode, for use in conjunction with an urological operative endoscopic instrument.

BACKGROUND OF THE INVENTION

In urology, there are two catagories of endoscopic instruments. The first category is diagnostic and is represented primarily by a cystoscope. The second category is operative which includes primarily the resectoscope and the visual urethrotome. The first category of instruments is not intended to include a manueverable part at the objective end of the instrument, that is, the end inside the patient. The instrument may have a catheterizing element, but its purpose is secondary to the observation purpose of the instrument and, consequently, the element is only poorly controlled and maneuvered.

The operative instruments, in distinction to the diagnostic instruments, include a working element which allows precise and controllable movement of a tool at the objective end of the instrument. In this fashion, the operative instrument provides for accurate cutting and fulguration inside the patient.

Because of the precision control with these endoscopic instruments, patients do not have to be cut open, and every year urologists perform several million operations, such as prostatectomies, removal of bladder tumors, removal of bladder stones, operations of the urethra, etc. In many of these situations, first a diagnosis is made using a cystoscope and at a later date the operation is performed. It has been common to give a general or spinal anesthetic at the time of the surgery. After the general anesthetic has taken effect, a resectoscope is introduced through the urethra and the operation is performed.

Because of the high cost of medical care, urologists are encouraged to perform certain of these operations on an out-patient basis, and if possible, under local anesthesia. The latter method not only reduces the cost of care by a considerable measure, but also removes the risk of a general or spinal anesthesia. Recently in endoscopic urological surgery, the application of local anesthesia has been facilitated by the introduction of an injection needle for use with a cystoscope. The cystoscopic injection needle is very helpful. Its application, however, is limited with the result that from a surgeon's point of view, the tool has numerous disadvantages. In particular, it is usable only with the observation instrument, that is, the cystoscope, with the result that there is very little maneuverability of the needle at the objective end of the instrument. Additionally, after application of the local anesthetic, it is necessary to remove the cystoscope from the patient and replace it with a resectoscope to perform the operative procedure of the operation. After the above multiple instrumentation and when the cutting and the fulguration has begun, if the anesthesia is not sufficient, or if additional areas of tissues are found that must be cut and burned, the resectoscope must be removed and the cystoscope reinserted to inject additional medication. Thereafter, naturally, the cystoscope again must be removed and the resectoscope again replaced in the patient. In this fashion, the patient's urethra may be severely tramatized. A further disdavantage is that the operator must hold the cystoscope with one hand and must direct the needle tip by way of the catheterizing element with his other hand. Since both hands are occupied, a second person is needed to inject the medication.

The cystoscopic injection needle is simply a hollow needle attached to a semi-rigid conduit element. The conduit element is attached to a luer lock for connection to a syringe. An injection needle in accordance with the present invention is not as simple, but it eliminates the disadvantages of the cystoscopic injection needle and, consequently, the indicated urological surgical method may be much simplified.

SUMMARY OF THE INVENTION

The present invention is directed to an injection needle for use with an endoscopic instrument of the type having a working element with means for clamping the injection needle or other tool thereto. The injection needle includes a hollow needle and a conduit to provide fluid communication between the needle and a forcing mechanism. The injection needle further includes mechanism for being held by the instrument clamping mechanism and mechanism for allowing the conduit to be directed away from the held mechanism.

More particularly, an injection needle in accordance with the present invention includes a hollow needle with a rigid or semi-rigid shaft attached thereto. A conduit element is fastened within the shaft to complete a fluid communication path from the needle to a forcing mechanism. In the case where the shaft is rigid, its free end which is clamped by the working element of the operative instrument, includes a slot through which the conduit element may extend and be deflected away from the clamping mechanism. A somewhat similar embodiment utilizes a semi-rigid shaft wherein the slot is formed by cutting halfway across the shaft and then longitudinally along the shaft so that the end portion of the shaft may be bent away from the thus cut portion or tab to direct the end portion and the conduit element therein to a luer lock and a forcing mechanism. The tab is then received by the clamp mechanism of the instrument. An injection needle with a semi-rigid shaft is particularly advantageous since it may be inserted into a resectoscope in an antegrade fashion whereas an injection needle with a rigid shaft must be inserted retrograde. Furthermore, with the cut portion of the shaft fitting together with the end portion, the shaft may function as a single semi-rigid shaft except when its end portion is bend away from the cut portion. In this fashion, the injection needle may be used in either an observation instrument like a cystoscope as described in the art or an operative instrument like the resectoscope.

Another embodiment of the present invention includes a mechanism for electrically connecting a conductive needle to an electrical connector within the instrument, the connector being connected to an electrical source as appropriate. In the case of a rigid shaft, the shaft itself may be electrically conductive with its clamped end in contact with the instrument connector. In the case of a semi-rigid shaft, flexible wires may run from the needle to a conductive end piece attached near the cut portion of the semi-rigid shaft. The conductive end piece then is clamped in contact with the instrument connector.

In yet another embodiment, a pair of shafts are held in a spaced, parallel relationship. A first shaft is conductive and is connected between the needle and the connector of the instrument. The second shaft is preferably nonconductive and encases the conduit element. The clamping mechanism of the instrument holds the end of the first shaft so that it is in contact with the electrical connector of the instrument. The second shaft is shorter than the first so that the conduit element may be deflected away from the working element of the instrument and attached to a luer lock and syringe. Alternatively, the second shaft may include a slot through which the catheterizing element may be deflected.

Thus, it is apparent that there are numerous embodiments which provide for the present injection needle to be held by the working element of an operative endoscopic instrument while at the same time allowing the conduit mechanism from the needle to be deflected away from the clamp mechanism of the working element for attachment to a syringe or other forcing mechanism. Each of the embodiments further provides for the additional feature of using the needle as an electrode.

The present needle is for use in an operative endoscopic instrument such as a resectoscope or a visual urethrotome, although at least one embodiment of the present invention may be used in a cystoscope as well. With the availability of the present injection needle, it may be suggested to urologists that the visual urethrotome sheath, which is of a diameter almost as small as the sheath of the cystoscope and not nearly as large as that of the resectoscope, be used in many patients wherein an endoscopic operation is expected. In this fashion, after observation and diagnosis with the visual urethrotome, if an operation is necessary and can be performed using local anesthesia, the local anesthetic may be injected through the present injection needle, which may be readily fitted in the instrument already in the patient. Thus, multiple instrumentations are unnecessary. Furthermore, during the course of cutting and fulguration, if more anesthesia is needed, the cutting tool can be replaced with the injection needle and adequate anesthesia obtained. Again, no change of instrument is necessary.

As opposed to an injection needle limited to a cystoscope, the present needle is designed for use with an operative endoscope like a resectoscope or a visual urethrotome which has a working element and so provides precise and well controlled maneuverability at the objective end (inside the patient) of the instrument. Injections can be given in the exact areas where they are needed. There are no uncontrollable movements of a sharp needle tip, thereby avoiding unnecessary tissue puncture, bleeding and resultant blocking of vision. Furthermore, since the operative endoscope, including the injection needle clamped to the working element, can be held and maneuvered with one hand, the surgeon himself can inject the medication in the exact amount desired with his other hand. A second person is not needed.

The present invention is further advantageous in that a modified version provides both the injection function and the cutting and fulguration function of an electrode. With this version, one instrument may not only provide for initial observation and diagnosis, but also for medication injection, and cutting and fulguration. Thus, a single instrument with a single tool may be used to perform both observation and a number of operative procedures. The present invention not only eliminates the disadvantages of the art, but also provides advantages and advances beyond anything previously available.

These advantages and other objects obtained this invention are further explained hereinafter and may be better understood by reference to the drawings which form a further part of this disclosure.

BRIEF DESCRIPTION OF THE DRAWINGS

FIG. 1 is a cross-sectional view of the injection needle-electrode in accordance with the present invention;

FIG. 2 is a detailed view in perspective of a portion of the tool shown in FIG. 1;

FIG. 3 is a detailed view in perspective, similar to FIG. 2, of an alternate embodiment;

FIG. 4 is a side elevational view of a further alternate embodiment;

FIG. 5 is a plan view of the tool of FIG. 4;

FIG. 6 is a cross-sectional view taken along 6—6 of FIG. 4;

FIG. 7 is a partial cross-sectional view of a resectoscope with an attached injection needle in accordance with the present invention; and FIG. 8 is a cross-sectional view taken along line 8—8 of FIG. 7 showing the clamping mechanism of the instrument shown in FIG. 7.

DETAILED DESCRIPTION OF THE PREFERRED EMBODIMENT

Referring now to the drawings wherein like reference numerals designate identical or corresponding parts throughout the several views, and more particularly to FIGS. 1 and 2, an injection needle-electrode is designated generally as 10. Tool 10 is comprised of a needle 12 fastened to a semi-rigid shaft 14 having a conduit element or flexible tube 16 extending therethrough. Flexible tube 16 is fastened to a luer lock 106 (see FIG. 7) for connection to a syringe (not shown). An end element 18 is either an integral part of shaft 14 or a separate part as shown in FIG. 1. The end element 18 is electrically connected to needle 12 by a plurality of wires 20. Thus, medication may be forced from a syringe through the conduit element 16 and shaft 14 to needle 12, or needle 12 may be used as an electrode which is electrically connected through wires 20 to end piece 18 which in turn is electrically connected to an electrical source.

More particularly, needle 12 is fastened at one end of shaft 14 in a conventional way. Shaft 14 is hollow and includes a slot 22 at a distance from the injection tip 24 of needle 12 approximately equal to the distance between the objective end 26 and the clamp mechanism 28 of instrument 30 (see FIG. 7).

Flexible tube 16 fits within the inside diameter of shaft 14 and extends at least beyond slot 22 toward needle 12. Flexible tube 16 may extend through shaft 14 to make contact with needle 12. Flexible tube 16 is fastened to shaft 14 in a conventional way. In this fashion, tube 16 and shaft 14 provide a conduit from the forcing mechanism such as a syringe (not shown) to needle 12.

End piece 18 provides the mechanism for attaching tool 10 to an operative instrument such as resectoscope 30 shown in FIG. 7. With end piece 18 crimped or otherwise attached to shaft 14 at the needle end of slot 22, end piece 18 may not only be held by clamping mechanism 28 of instrument 30, but shaft 14 and tube 16 may be bent away from clamping mechanism 28 to allow connection of tube 16 to a syringe. End piece 18 has a cylindrical portion 32 which has an inside diameter approximately the same as the outside diameter of shaft 14. Cylindrical portion 32 is fastened to shaft 14. A semi-cylindrical portion 34 extends away from portion 32 and has inside and outside diameters similar to shaft 14. Semi-cylindrical portion 34 extends sufficiently far to mate with shaft 14 and fill slot 22 when shaft 14 is straightened. Semi-cylindrical portion 34 is the element of tool 10 held by clamping mechanism 28.

One or more wires 20 run between electrically conductive needle 12 and electrically conductive end piece 18. Wires 20 are flexible and are attached to needle 12 and to end piece 18 by soldering or with other appropriate mechanism. Wires 20 are preferably located between tube 16 and shaft 14.

Alternatively, slot 22 may be formed by cutting halfway through shaft 14 at the end 36 of slot 22 farthest from needle 12 and then cutting toward needle 12 for the length of the desired slot. In this fashion, an end piece 18 is not used but rather shaft 14 may be bent away from the cut portion, which cut portion may then be held by the clamping device 28 of instrument 30. With this type of embodiment, tool 10 could not function as an electrode since it would neither have a conductive end piece 18 nor wires 20. Such embodiment, however, is versatile nevertheless since it may be folded together at slot 22 and used in a cycstoscope, or it may be used in a resectoscope or other operative endoscopic instrument by clamping the cut portion and bending shaft 14 at slot 22.

In another embodiment as shown in FIG. 3 where elements equivalent to those of the previously described embodiment are designated by the same numbers only with primes, shaft 14' is rigid and has an end 38 similar to the semi-cylindrical portion 34 of end piece 18. Slot 22' is cut in the end of shaft 14' adjacent to end portion 38 to provide a mechanism for flexible tube 16' to be bent away from end portion 38 which is held by clamping mechanism 28 of instrument 30. By making shaft 14' conductive, tool 10' may be used as an electrode. With this embodiment, it is necessary to have a nonconductive coating or shrink tubing 40 about shaft 14' except for the very end of portion 38 which makes contact with electrical connector 42 in instrument 30.

A further embodiment is shown in FIGS. 4-6. Tool 10" includes a pair of parallel, spaced-apart shafts 44 and 46. A clamp element 48 holds one end of shafts 44 and 46 separated and in proper parallel relationship. Cylinder 50 holds the other end. Clamp 48 is a single piece of spring metal formed to have a base 52 with semi-cylindrical edges 54 which fit about each of shafts 44 and 46. Each end of clamp 48 includes tabs 56 which are crimped almost completely about shafts 44 and 46. Between the end tabs, sides 58 rise away from shafts 44 and 46 and are formed arcuately to receive the portion of the endoscopic instrument to which tool 10" is to be clamped.

Cylinder 50 has an inside diameter sized to receive a tubular portion at the objective end of an endoscopic instrument. One end of cylinder 50 includes a flat member 60 extending perpendicularly away from cylinder 50. Each of shafts 44 and 46 are located on either side of member 60 and soldered or otherwise appropriately fastened. Needle 12" is soldered or otherwise appropriately fastened to the other end of cylinder 50. Needle 12" is centered on a line midway between shafts 44 and 46 and parallel with them.

A conduit element or flexible tube 16" extends through shaft 46 to its end near one end of cylinder 50 and then continues to needle 12" to which it is appropriately attached. As shown in FIG. 4, a short shaft 59 holds needle 12" at one end and tube 16" at the other end to provide the appropriate fastening mechanism.

Clamp 48 and cylinder 50 provide attachment points for tool 10" for the particular instrument for which this embodiment is designed. The dual shafts 44 and 46 give tool 10" stability. Shaft 44 is longer than shaft 46 and may be clamped to the working element as appropriate. Shaft 46 is shorter to allow flexible tube 16" to bend away from the clamping mechanism so as to be fastened to a syringe. For use as an electrode, needle 12" and shaft 44 are conductive while the other elements are preferably nonconductive. A wire 61 is appropriately fastened between shaft 44 and needle 12" to complete the electrical path. The held end of shaft 44 makes contact with an appropriate connector in the working element of the endoscopic instrument.

In use, the injection needle-electrode of the present invention is a tool which may be designed in a number of embodiments for use in various endoscopic instruments, particularly those applicable to urological surgery. One of the embodiments indicated hereinbefore, is also usable in a cystoscope, an observation urological instrument. FIGS. 7 and 8 show a tool 10 used in a representative urological operative instrument 30, namely a resectoscope.

Instrument 30 includes an optical assembly 62 having a telescope tube 64 with an eyepiece 66 at its proximate end and an objective lens 68 at its distal end. A light source (not shown) may be connected at nipple 70 for transmission of light through a bundle of fiber-optic rods 72 to illuminate the field of view.

Optical assembly 62 is attached to the working element 74 with thumbscrew 76. Sheath 78 is frictionally fastened to working element 74 and released by turning thumbscrew 80. Sheath 78 is tubular and includes telescope tube 64 and provides additional space for the passage of accessory tools such as tool 10. Appropriate connections may be made at tube 82 to direct irrigating fluid into and through sheath 78.

Working element 74 includes a body 84 and a header 86 connected together by a frame 88 including a pair of parallel rods 90. Body 84 and header 86 are further connected by leaf spring 92. Body 84 may be movably guided on rods 90 by forcing body 84 toward header 86. Leaf spring 92 energizes and acts to force a return of body 84 to its original position when the force at finger loop 94 is released.

As shown in FIG. 8, body 84 includes the clamp mechanism 28 for grasping tool 10 and moving it axially whenever body 84 is moved along rods 90. Clamping mechanism 28 includes a threaded rod 98 which moves grip element 100 with respect to grip element 102. The shaft 14 of tool 10 extends through sheath 78 and an opening in header 86 so that the end portion 34 may be inserted into passage 104 and clamped by gripper elements 100 and 102.

As shown in FIG. 7, body 84 also includes an electrical connector 42 having a conductive portion extending into body 84 so that the shaft or the end element of tool 10 may contact the connector allowing tool 10 to function as an electrode.

To install a tool 10 in resectoscope 30, instrument 30 may be in or out of the patient. Tool 10 is inserted in a retrograde fashion by passing needle 12 and shaft 14 through header 86. With end portion 34 between header 86 and body 84, shaft 14 is bent at slot 22 so that it extends away from body 84 and may be connected to luer lock 106 for connection to a syringe. The portion of shaft 14 within sheath 78 is then moved toward body 84 so that end portion 34 extends into passage 104 allowing end portion 34 to be clamped by clamping mechanism 28. By extending tool 10 into passage 104 so that end portion 34 of end piece 18 contacts connector 42, tool 10 may be used as an electrode when connector 42 is appropriately connected to an electrical energy source. Tool 10 is now operable by instrument 30 simply by operating working element 74 and moving the tip of needle 12 longitudinally within the objective field of view of instrument 30.

Tool 10 is removed from resectoscope 30 by reversing the hereinbefore described steps and may be so removed while resectoscope 30 is either in or out of a patient.

Tool 10' must be inserted antegrade through header 86. Consequently, such embodiment may not be installed or removed, while instrument 30 is in a patient.

Thus, the injection needle-electrode of the present invention is a tool usable in an operative endoscopic instrument such as a resectoscope for both injecting and as an electrode. A portion of the shaft of the tool may be held by the working element of the instrument thereby providing that when the working element is moved, the tip of the needle may be observed through the optical assembly. An appropriate embodiment may be installed and removed while an instrument is in place within a patient. Other embodiments are usable in other instruments to provide greater versatility.

In spite of the various exemplary embodiments, and the numerous characteristics and advantages set forth, together with details of structure and function, it is to be understood that the disclosure of the present invention is illustrative. Thus, changes made, especially in shape, size, and arrangement, to the full extent extended by the general meaning of the terms in which the appended claims are expressed, are understood to be within principle of the invention.

What is claimed:

1. A tool for use with an endoscopic instrument for applying fluid from forcing means, said instrument having an eyepiece at a proximal end and a sheath at a distal end, said instrument further including a working element with a body and a header, said body being guidably movable toward and away from said header, said sheath and said header including passages for receiving said tool, said body including clamping means for holding a portion of said tool, said tool comprising:
   a hollow needle with a tip and an opposite end portion, said needle for projecting partially from the sheath of said endoscopic instrument when said body of said instrument is moved toward said header;
   extending means for being received by the clamping means of the body of said instrument, said extending means being connected to said needle;
   flexible conduit means for directing fluid from the fluid forcing means to an end portion positioned for fluid communication with said needle; and
   means for encasing the end portions of said conduit means and said needle, said encasing means extending from the end portion of said needle when it projects partially from the sheath of said instrument to between said body and said header, said extending means extending beyond said encasing means to the clamping means of the body, said encasing means including means for providing said conduit means to be bent between said header and said body so that said conduit means may be directed away from said instrument;
   whereby said flexible conduit means may be directed from between said header and said body away from said instrument to said forcing means thereby providing fluid communication from said forcing means to said needle, through said conduit means and said encasing means, while providing operable connection at said extending means between said tool and said instrument.

2. A tool for use with an endoscopic instrument for applying fluid from forcing means, comprising:
   a hollow needle;
   a semi-rigid, hollow shaft having a first transverse cut approximately halfway therethrough along said shaft to form first and second end portions separated by said first cut, the first end portion of said shaft being attached to said needle, said shaft further having a second cut longitudinally along said shaft from said first cut to define a tab attached to said first end portion with said second end portion being bendable away from said tab, said tab for being held by said instrument;
   a flexible tube attached to said shaft and in fluid communication through said shaft with said needle, said tube for receiving liquid from forcing means to apply through said needle to body tissue;
   whereby said second end portion of said shaft and said tube therein may be bent away from said tab so that said instrument may hold said tool at said tab.

* * * * *